US006262067B1

(12) United States Patent
Allen et al.

(10) Patent No.: US 6,262,067 B1
(45) Date of Patent: Jul. 17, 2001

(54) POLYMORPHS OF A CRYSTALLINE AZO-BICYCLO 2,2,2 OCT-3-YL AMINE DIHYDROCHLORIDE AND THEIR PHARMACEUTICAL COMPOSITIONS

(75) Inventors: Douglas J. M. Allen, New London; Troy Anthony Appleton, East Lyme; Michael Jon Gumkowski, Old Lyme; David Joseph Muehlbauer, North Stonington; Timothy Norris, Gales Ferry, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/564,528

(22) Filed: May 4, 2000

Related U.S. Application Data

(60) Provisional application No. 60/140,233, filed on Jun. 22, 1999.

(51) Int. Cl.[7] ....................... A61K 31/435; A61K 31/445; C07D 453/02; A61P 1/08
(52) U.S. Cl. ............................................. 514/305; 546/133
(58) Field of Search .............................. 514/305; 546/133

(56) References Cited

U.S. PATENT DOCUMENTS 5,939,433 * 8/1999 Ito et al. .............................. 514/305

OTHER PUBLICATIONS

Hesketh, P.J. et al.: Randomized phase II study of the Neurokinin 1 receptor antagonist CJ–11,974 in the control of Cisplatin–induced emesis. J. Clin. Oncol. vol. 17, pp. 338–343, Jan. 1999.*
Biles, J.A.: Crystallography. Part II. J. Pharm. Sci. vol. 51, pp. 601–617, Jul. 1962.*

* cited by examiner

Primary Examiner—Charanjit S. Aulakh
(74) Attorney, Agent, or Firm—Peter C. Richardson; Paul H. Ginsburg; Jolene W. Appleman

(57) ABSTRACT

Two crystalline polymorphic forms of (2-Benzhydryl-1-azo-bicyclo(2.2.2]Octyl-3-yl)-(5-iso-propyl-2-methoxybenzyl) amine dihydrochloride dihydrate are Form I and Form II. The pharmaceutical composition containing at least are of these polymorphs has advantageous stability for formulation to treat emesis in patients receiving chemotherapy. The administration of this pharmaceutical composition is conventional oral by preferably tablet or capsule or intravenous. A method of making Forms I and II is also disclosed.

21 Claims, No Drawings

POLYMORPHS OF A CRYSTALLINE AZO-BICYCLO 2,2,2 OCT-3-YL AMINE DIHYDROCHLORIDE AND THEIR PHARMACEUTICAL COMPOSITIONS

The application claims the benefit of U.S. Provisional Patent Application No. 60/140,233 filed Jun. 22, 1999.

This invention is directed to certain polymorphs and forms of crystalline (2-Benshydryl-1-azo-bicyclo 2,2,2 oct-3yl)-(5isopropyl-2-methoxybenzyl)-amine dihydrochloride (hereafter the dihydrochloride salt) and their pharmaceutical compositions. The dihydrochloride salt is a CNS active NK-1 receptor antagonist and this invention is directed to methods of treating conditions effected or facilitated by a decrease in substance P mediated neuro-transmission. This invention is also directed to a substance P antagonist which is evaluated for acute and delayed anti-emetic efficacy in a mammal including humans receiving chemotherapy. Treating is defined here as preventing and treating.

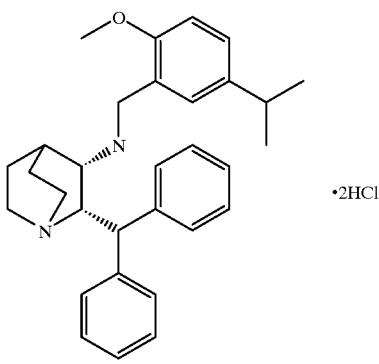

•2HCl

U.S. Pat. No. 5,393,762 and U.S. Ser. No. 08/816,016 both incorporated by reference, describe pharmaceutical compositions and treatment of emesis using NK-1 receptor antagonists. The crystalline anhydrous dihydrochloride is hygroscopic at humidities of about 52% or greater and forms dihydrates. The dihydrates do not readily dehydrate when exposed to low relative humidity of about 33% or less.

SUMMARY OF THE INVENTION

The present invention relates to the anhydrous dihydrochloride of (2-Benzhydryl-1-azo-bicyclo 2,2,2oct-3-yl)-(5-isoproyl-2-methoxybenzyl)-amine, the dihydrochloride dihydrate and its two polymorphs.

In one embodiment of the invention, the anhydrous dihydrochloride is a crystalline hygroscopic single form. The morphology of the anhydrous dihydrochloride is rods with particle size of about 5 to 30 $\mu$m yielding birefringence. A differential scanning calorimetry (DSC) thermogram gave a sharp endotherm with an onset at 224° C., Tmax at 236° C. and a $\Delta$Hf of 32.8 cal/gram.

In two other embodiments, the dihydrochloride dihydrate is in Form I or Form II. Form I is characterized by the X-ray diffraction pattern below:

| Dihydrochloride Dihydrate Form I | | | | | | | | |
|---|---|---|---|---|---|---|---|---|
| Peak No. | 1 | 2 | 3 | 4 | 5 | 6 | 7 | 8 |
| d space | 17.2 | 9.5 | 8.4 | 6.9 | 4.9 | 4.4 | 3.9 | 3.5 |

Form I of the dihydrochloride dihydrate is a nonhydroscopic single form and discloses a Differential Scanning Calorimetry thermogram with onsets at about 150° C. and 230° C. Form I has a solubility of about 110 to 120 milligrams per milliliter. The crystalline habit of Form I is flakes with a size range of about 30 $\mu$m to 60 $\mu$m.

Form II is characterized by the X-ray diffraction pattern below:

| Dihydrochloride Dihydrate Form II | | | | | | | | |
|---|---|---|---|---|---|---|---|---|
| Peak No. | 1 | 2 | 3 | 4 | 5 | 6 | 7 | 8 | 9 |
| d space | 11.3 | 8.8 | 7.5 | 6.4 | 4.9 | 4.5 | 3.8 | 3.7 | 3.0 |

Form II is a lower energy, more stable form than Form I. Form It has a solubility of about 390–400 milligrams per milliliter. Form II's crystalline habit is flakes of about 15 to 25 $\mu$m.

The method of making the polymorphic Form I of the dihydrochloride dihydrate comprises stirring at ambient temperature the anhydrous dihydrochloride in an organic solvent containing about 0.5 to 2.5% water for about 15 to 25 hours to effect crystallization. The organic solvents are selected from ethyl or isopropyl alcohol, ethyl acetate, acetonitrile, tetrahydrofuran and acetone all containing about 0.5% to 2.5% water.

The method of making the polymorphic Form II of the dihydrochloride dihydrate comprises stirring Form I or the anhydrous dihydrochloride at ambient temperature in an organic solvent containing about 3 to 5% water for about 15 to 25 hours to effect crystallization. The solvents are chosen from ethyl acetate with about 5% water, tetrahydrofuran with about 5% water, acetone with about 5% water and acetonitrile with about 5% water.

Another aspect of the invention relates to a pharmaceutical composition having pharmaceutical activity which comprises at least one of polymorphic Forms I and II of the dihydrochloride dihydrate and the anhydrous dihydrochloride in the treatment of emesis. A method of treating emesis comprises administering to a subject in need of treatment, an antiemetic effective amount of Form I or II or the anhydrous dichloride.

DETAILED DESCRIPTION OF THE INVENTION

Polymorphic Form I of the dihydrochloride dihydrate may be formed by stirring the anhydrous form of the compound in an appropriate organic solvent containing 0.5% to 2.5% water for a suitable time to effect the crystallizaton. Appropriate solvents may include the following: ethyl or isopropyl alcohol, ethyl acetate, acetonitrile, tetrahydrofuran, and acetone, all containing between 0.5% to 2.5.% water.

Polymorphic Form II may be formed by stirring either Form I or the anhydrous form of the dihydrochloride in an appropriate organic solvent containing 3% to 5% water for a suitable time to effect the crystallization. Appropriate solvents may include the following; Ethyl acetate containing 3.5% water, tetrahydrofuran (THF) containing 5% water, acetone containing 5% water and water.

The "wet" THF bridge resulted in complete conversion to Form II. When Form I is slurried in THF with less than 2% $H_2O$ there is no conversion to Form II. When Form I is slurried in THF with about 3% to 5% $H_2O$, the conversion is to Form II. When Form I is slurried in THF with >5% $H_2O$, solubility increases dramatically due to the high aqueous solubility.

Table I below shows an ambient polymorph screen with wet solvents:

Table I

| Polymorph Isolated | Starting Form | Solvent | Isolation Temperature | Isolation Method |
|---|---|---|---|---|
| Form I | Form I | IPO/5% H₂O | ambient | Slurry |
| Form II | Form I | Ethyl Acetate/3.5% H₂O | ambient | Slurry |
| Form I | Form I | Acetonitrile/5% H₂O | ambient | Slurry |
| Form II | Form I | Tetrahydrofuran/5% H₂O | ambient | Slurry |
| Form II | Form I | Acetone/5% H₂O | ambient | Slurry |
| Form II | Form I | H₂O | ambient | Slurry solutions seeded with Form II |

Table II below gives a polymorph characterization of Form I and Form II:

TABLE II

| Assay | Form I | Form II |
|---|---|---|
| Combination Analysis | dihydrochloride, dihydrate | dihydrochloride, dihydrate |
| Karl Fisher | 7.08% | 7.10% |
| Powder X-ray | Form I | Form II |
| Fusion Microscopy | Slow water loss (50° C.–75° C.) | Sharp water loss ~100° C. |
| VTI (% H₂O absorbed) | 0.8% wt. | 0.4% wt. |
| Aqueous Intrinsic Solubility | >648 mg/ml. | <329 mg. ml |
| Aqueous Equilibrium | >1155 mg/ml. | 395 mg/ml. |
| Crystal Habit | flake, ~30 × 60 μm | flake, ~15 × 25 μm |
| TGA/DTA | Water loss 30° C.–110° C., two events prior to degradation @ 194° C. | Water loss 30° C.–100° C. with apparent degradation @ 178° C. |
| Differential Scanning Calorimetry (DSC) | Event @ ~175° C. then degradation @ ~230° C. Water loss is undetected, | Hydrates Off @ ~130° C. and ~155° C., possible re-cryst @ ~170° C., possible anhydrous melt @ 240° C., then degradation |

EXAMPLE 1
Preparation of crystalline anhydrous dihydrochloride

A mixture of Benshydryl-1-azo-bicyclo 2,2,2 oct-3yl)-(5-isopropyl-2-methoxybenzyl)-amine dihydrochloride dihydrate (10.0 g) in ethylacetate (100 ml) was heated at reflux in a Dean and Start apparatus for 23 hours. The reaction was cooled to room temperature and stirred for 1 hour. The solid was removed by filtration, washed with ethylacetate (20 ml) and dried in vacuo at 55° C. with a nitrogen bleed for 24 hours to give the anhydrate as a white solid.

EXAMPLE 2
Preparation of the crystalline dihydrate Form I

A 53.2 Kg portion of the 1-R-(–)camphorsulfonate salt is dissolved in a mixture of 266 L of water and 266 L of methylene chloride. The pH is adjusted to a range of 10–14 with 5.08 L of 50% sodium hydroxide. The product rich methylene chloride layer is separated and back washed with 53.2 L of water. The methylene chloride is concentrated atmospherically and is displaced by tetrahydrofran (668.4 L). A 13.9 L portion of 12 N hydrochloric acid is added to the tetrahydrofuran and the mixture is heated to reflux for 3 hours. The resulting slurry is cooled to 25° C. to 30° C., granulated for 1 hour and the Form 1 crystal is collected by filtration.

EXAMPLE 3
Preparation of the crystalline dihydrate Form II

A 25 Kg portion of Form I dihydrate is slurried in THF/3%–5% water (3001 L THF+101 L water) at reflux (~64° C.) for 48 hours. The slurry is cooled to 25° C. to 30° C., granulated for 1 hour and the Form II collected by filtraton.

What is claimed is:

1. The crystalline forms of (2-Benzhydryl-1-azo-bicyclo [2.2.2]oct-3-yl)-(5-isopropyl-2-methoxy-benzgi)-amine dihydrochloride having the formula

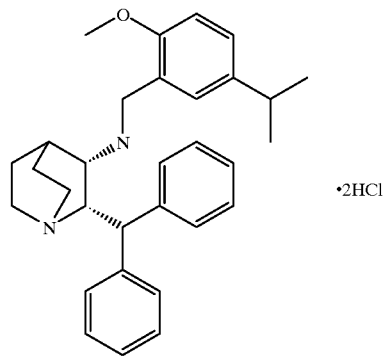

wherein said crystalline form is selected from the group consisting of
a) a hygroscopic dihydrochloride anhydrous form;
b) a nonhygroscopic dihydrochloride dihydrate, Form I polymorph exhibiting the x-ray powder diffraction pattern

| Peak No. | 1 | 2 | 3 | 4 | 5 | 6 | 7 | 8 |
|---|---|---|---|---|---|---|---|---|
| d space | 17.2 | 9.5 | 8.4 | 6.9 | 4.9 | 4.4 | 3.9 | 3.5 | and
c) a nonhygroscopic dihydrochloride dihydrate, Form II polymorph exhibiting the x-ray powder diffraction pattern

| Peak No. | 1 | 2 | 3 | 4 | 5 | 6 | 7 | 8 | 9 |
|---|---|---|---|---|---|---|---|---|---|
| d space | 11.3 | 8.8 | 7.5 | 6.4 | 4.9 | 4.5 | 3.8 | 3.7 | 3.0 |

2. The anhydrous dihydrochloride according to claim 1 wherein the anhydrous dihydrochloride crystalline habits are rods.

3. The anhydrous dihydrochloride according to claim 2 wherein said rods have a particle size of about 5 to 30 μm.

4. The anhydrous dihydrochloride according to claim 1 wherein a differential scanning calorimetry thermogram gave a sharp endothern with an onset at about 224° C., temperature maximum at about 236° C. and a ΔHf of about 32.8 cal/gram.

5. The nonhygroscopic dihydrochloride dihydrate polymorph according to claim 1 wherein Form I's crystalline habit are flakes.

6. The dihydrochloride dihydrate polymorph according to claim 5 wherein Form I's crystalline flake size is about 30 μm to 60 μm.

7. The dihydrochloride dihydrate polymorph according to claim 1, wherein Form I's solubility is about 640–1160 mg/ml.

8. The dihydrochloride dihydrate polymorph according to claim 1 wherein Form I has a differential scanning calorimetry thermogram with onsets at about 175° C. and 230° C.

9. The dihydrochloride dihydrate polymorph according to claim 1, wherein Form II has a solubility of about 390 to 400 mg/ml.

10. The dihydrochloride dihydrate polymorph according to claim 1 wherein Form II's crystalline habit are flakes.

11. The Form II polymorph according to claim 10 wherein the crystalline flakes have a size range of about 15 to 25 μm.

12. The dihydrochloride dihydrate polymorph according to claim 1 wherein Form II has a solubility of about 390 to 400 mg/ml.

13. A pharmaceutical composition having substance P antagonist activity comprising at least one of the polymorphic Forms I or II according to claim 1, in an amount effective in the treatment of emesis and a pharmaceutically acceptable carrier.

14. A method of treating emesis which comprises administering to a subject in need of treatment an antiemetic effective amount of the polymorphic Form I of the compound according to claim 1.

15. A method of treating emesis which comprises administering to a subject in need of treatment an antiemetic effective amount of the polymorphic Form II of the compound according to claim 13.

16. A pharmaceutical composition having substance P antagonist activity comprising the anhydrous dihydrochloride according to claim 1, in an amount effective in the treatment of emesis, and a pharmaceutically acceptable carrier.

17. A method of treating emesis which comprise administering to a subject in need of treatment an antiemetic effective amount of the anhydrous dihydrochloride of the compound according to claim 16.

18. A method of making crystalline dihydrochloride dihydrate polymorphic Form I of the anhydrous dihydrochioride of (2-Benzhydryl-1-azo-bicyclo 2,2,2 Oct-3-yl)-(5-isopropyl-2-methoxybenzyl)-amine comprising stirring at ambient temperature the anhydrous dihydrochloride in an organic solvent containing about 0.5 to 2.5% water for about 15–25 hours to effect crystallization.

19. A method of claim 18 wherein the organic solvents are selected from ethyl alcohol, isopropyl alcohol, ethyl acetate, acetonitrile, tetrahydrofuran and acetone.

20. A method of making crystalline dihydrochloride dihydrate polymorphic Form II of the anhydrous dihydrochloride of (2-Benzhydryl-1-azo-bicyclo 2,2,2Oct-3-yl)-(5-isopropyl-2-methoxybenzyl)-amine comprising stirring at ambient temperature Form I of the dihydrochloride dihydrate or the anhydrous dichlorate in an organic solvent containing about 3 to 5% water for about 15 to 25 hours to effect crystallization.

21. The method of claim 20 wherein the organic solvents are chosen from ethyl acetate with about 3.5% water, tetrahydrofuran with about 5% water, acetone with about 5% water and acetonitrile with about 5% water.

\* \* \* \* \*

UNITED STATES PATENT AND TRADEMARK OFFICE
CERTIFICATE OF CORRECTION

PATENT NO.   : 6,262,067 B1
DATED        : July 17, 2001
INVENTOR(S)  : Douglas J. M. Allen et al.

It is certified that error appears in the above-identified patent and that said Letters Patent is hereby corrected as shown below:

Column 5,
Line 11, please cancel claim 12.
Line 14, please replace claims 13-21 with claims 12-20 as follows:

12. A pharmaceutical composition having substance P antagonist activity comprising at least one of the polymorphic Forms I or II according to claim 1, in an amount effective in the treatment of emesis and a pharmaceutically acceptable carrier.

13. A method of treating emesis which comprises administering to a subject in need of treatment an antiemetic effective amount of the polymorphic Form I of the compound according to claim 1.

14. A method of treating emesis which comprises administering to a subject in need of treatment an antiemetic effective amount of the polymorphic Form II of the compound according to claim 12.

15. A pharmaceutical composition having substance P antagonist activity comprising the anhydrous dihydrochloride according to claim 1, in an amount effective in the treatment of emesis, and a pharmaceutically acceptable carrier.

16. A method of treating emesis which comprise administering to a subject in need of treatment an antiemetic effective amount of the anhydrous dihydrochioride of the compound according to claim 15.

17. A method of making crystalline dihydrochloride dihydrate polymorphic Form I of the anhydrous dihydrochioride of (2-Benzhydryl-1-azo-bicyclo 2,2,2 Oct-3-yl)-(5-isopropyl-2-methoxybenzyl)-amine comprising stirring at ambient temperature the anhydrous dihydrochloride in an organic solvent containing about 0.5 to 2.5% water for about 15-25 hours to effect crystallization.

UNITED STATES PATENT AND TRADEMARK OFFICE
CERTIFICATE OF CORRECTION

PATENT NO. : 6,262,067 B1
DATED : July 17, 2001
INVENTOR(S) : Douglas J. M. Allen et al.

It is certified that error appears in the above-identified patent and that said Letters Patent is hereby corrected as shown below:

18. A method of claim 17 wherein the organic solvents are selected from ethyl alcohol isopropyl alcohol, ethyl acetate, acetonitrile, tetrahydrofuran and acetone.

19. A method of making crystalline dihydrochloride dihydrate polymorphic Form II of the anhydrous dihydroclioride of (2-Benzhydryl-1-azo-bicyclo 2,2,2Oct-3-yl)-(5-isopropyl-2-methoxybenzyl)-amine comprising stirring at ambient temperature Form I of the dihydrochloride dihydrate or the anhydrous dichloride in an organic solvent containing about 3 to 5% water for about 15 to 25 hours to effect crystallization.

20. The method of claim 19 wherein the organic solvents are chosen from ethyl acetate with about 3.5% water, tetrahydrofuran with about 5% water, acetone with about 5% water and acetonitrile with about 5% water.

Signed and Sealed this

Sixteenth Day of September, 2003

JAMES E. ROGAN
*Director of the United States Patent and Trademark Office*